United States Patent
Park et al.

(10) Patent No.: US 7,411,200 B2
(45) Date of Patent: Aug. 12, 2008

(54) U.V. STERILIZER FOR DENTAL HANDPIECE

(75) Inventors: Heungsik Park, Busan (KR); Mansu Jang, Seoul (KR)

(73) Assignee: G.P. Co., Bucheon (KR)

( * ) Notice: Subject to any disclaimer, the term of this patent is extended or adjusted under 35 U.S.C. 154(b) by 230 days.

(21) Appl. No.: 10/587,774

(22) PCT Filed: Jan. 27, 2005

(86) PCT No.: PCT/KR2005/000219

§ 371 (c)(1),
(2), (4) Date: Jul. 28, 2006

(87) PCT Pub. No.: WO2005/072782

PCT Pub. Date: Aug. 11, 2005

(65) Prior Publication Data

US 2007/0160950 A1    Jul. 12, 2007

(30) Foreign Application Priority Data

Jan. 31, 2004   (KR)   .................. 10-2004-0006422
Apr. 7, 2004    (KR)   .................. 10-2004-0023796

(51) Int. Cl.
*A61C 1/00*    (2006.01)
*A61L 2/10*    (2006.01)

(52) U.S. Cl. .................. 250/455.11; 422/24; 433/29; 250/461.1

(58) Field of Classification Search ............ 250/455.11, 250/461.1; 422/24; 433/29
See application file for complete search history.

(56) References Cited

U.S. PATENT DOCUMENTS 5,185,532 A * 2/1993 Zabsky et al. .......... 250/455.11

FOREIGN PATENT DOCUMENTS

| JP | 58-193934 | 12/1983 |
| JP | 63-186654 | 8/1988 |
| JP | 63-166238 | 10/1988 |
| JP | 2003-116969 | 4/2003 |
| KR | 1019960010742 | 8/1996 |

\* cited by examiner

*Primary Examiner*—Nikita Wells
(74) *Attorney, Agent, or Firm*—John K. Park; Park Law Firm

(57) ABSTRACT

Disclosed herein is a sterilizer used at dental clinics to sterilize handpieces by the irradiation of ultraviolet rays. When inserting a contaminated handpiece into a sterilizer, an ultraviolet barrier is opened confirming the approach of the handpiece by a sensor. After the insertion of the handpiece, the ultraviolet barrier is closed, then ultraviolet lamps are turned on for a pre-determined time and then turned off, and the ultraviolet barrier is opened again. After the withdrawal of the handpiece, the ultraviolet barrier is closed. The handpiece is not contacted with the outside of the sterilizer, preventing the handpiece from being contaminated again by the sterilizer, and the leakage of the ultraviolet rays is prevented.

15 Claims, 5 Drawing Sheets

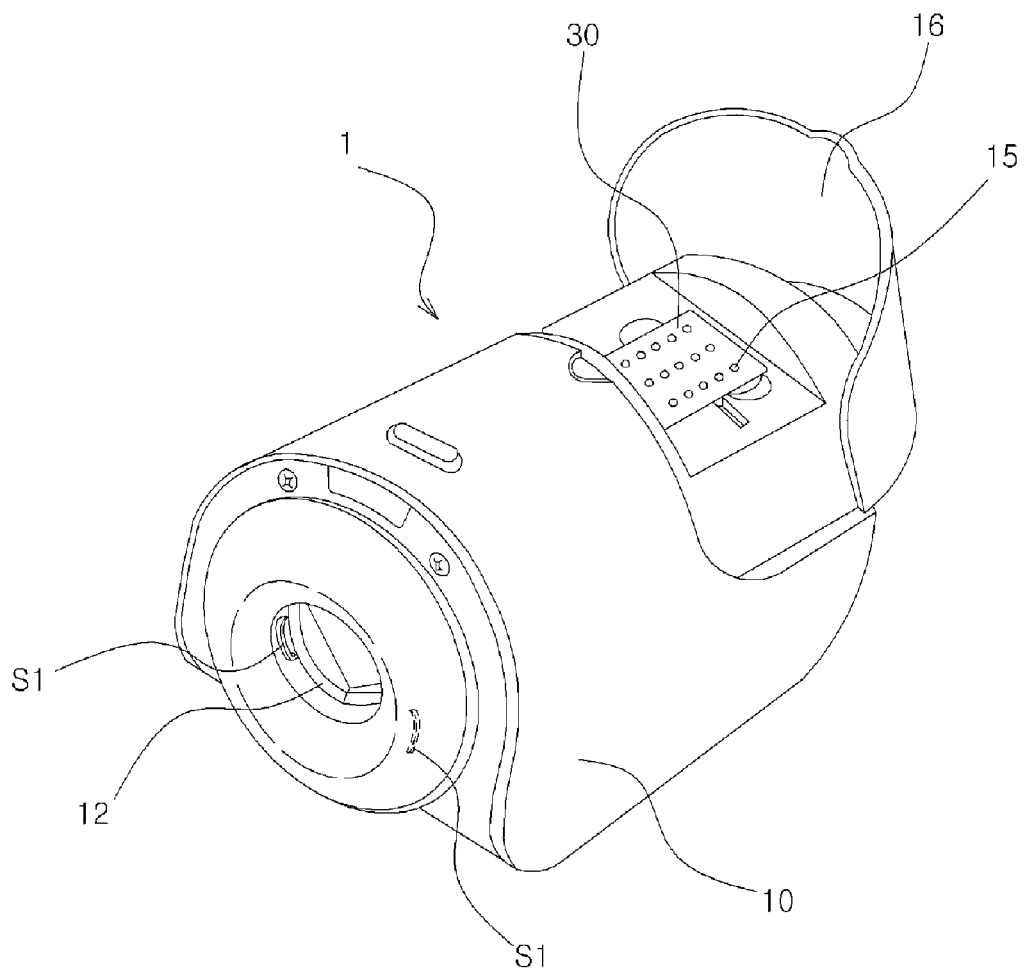
[Fig. 1]

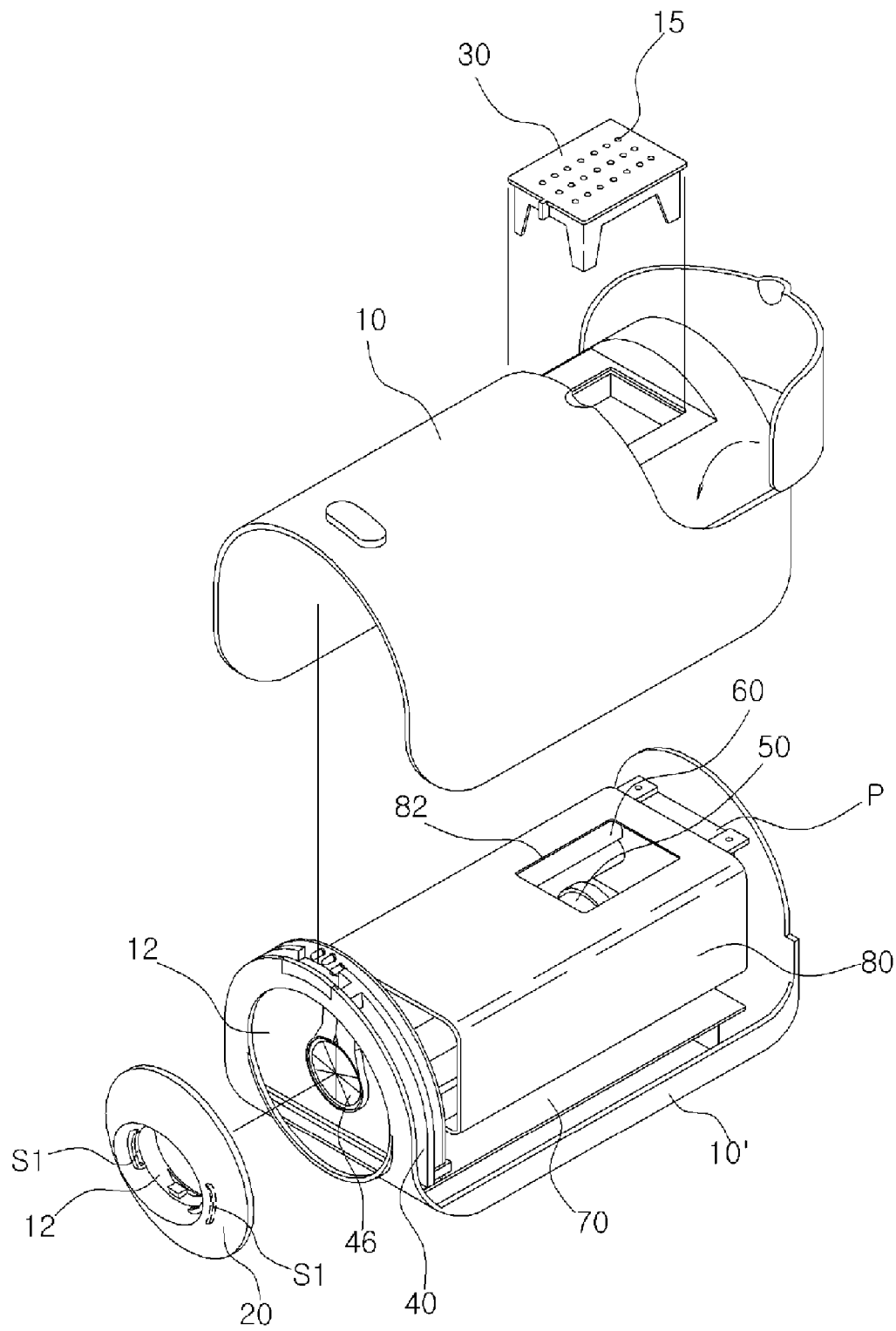
[Fig. 2]

[Fig. 3]
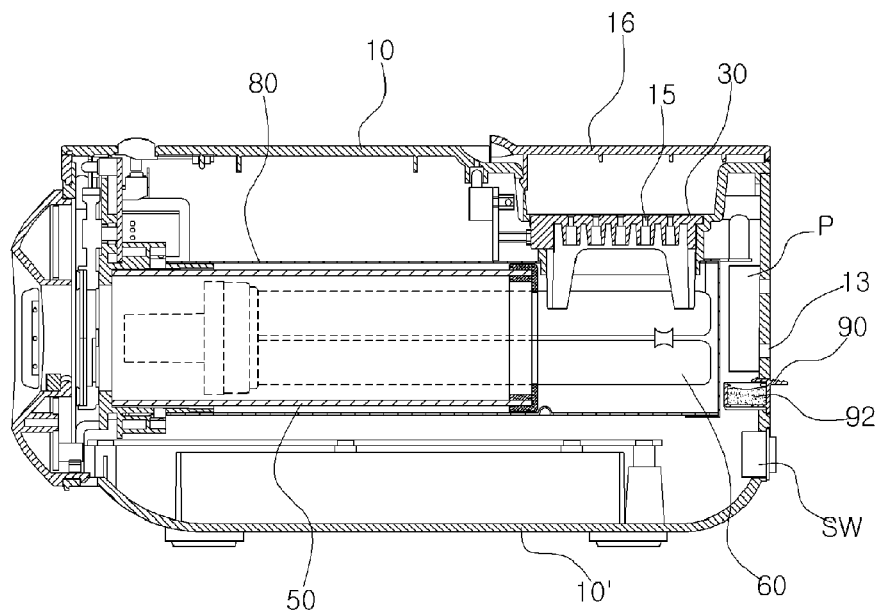
[Fig. 4]
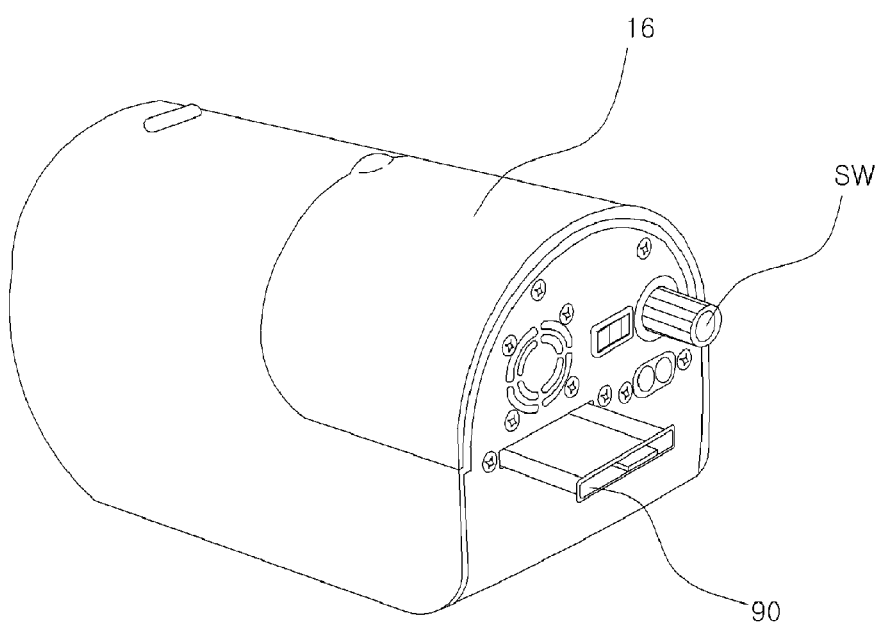

[Fig. 5]
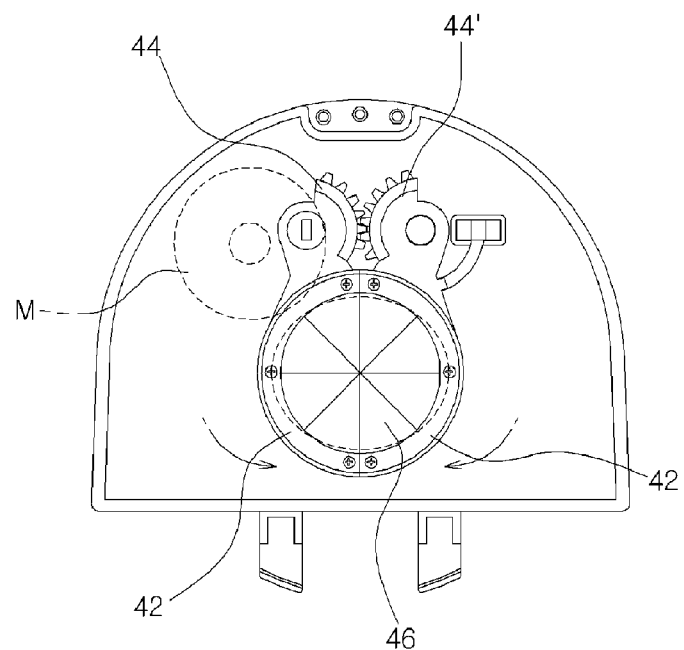
[Fig. 6]
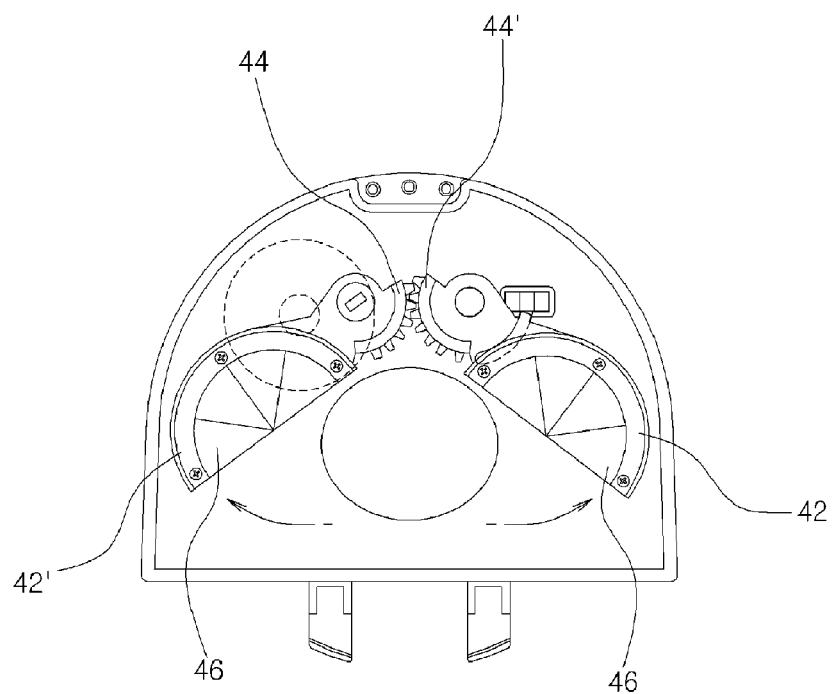

[Fig. 7]
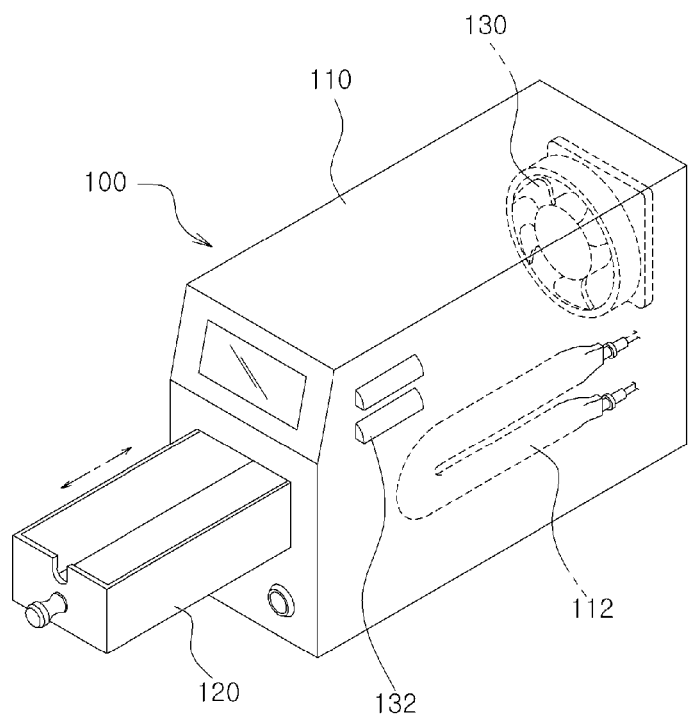
[Fig. 8]
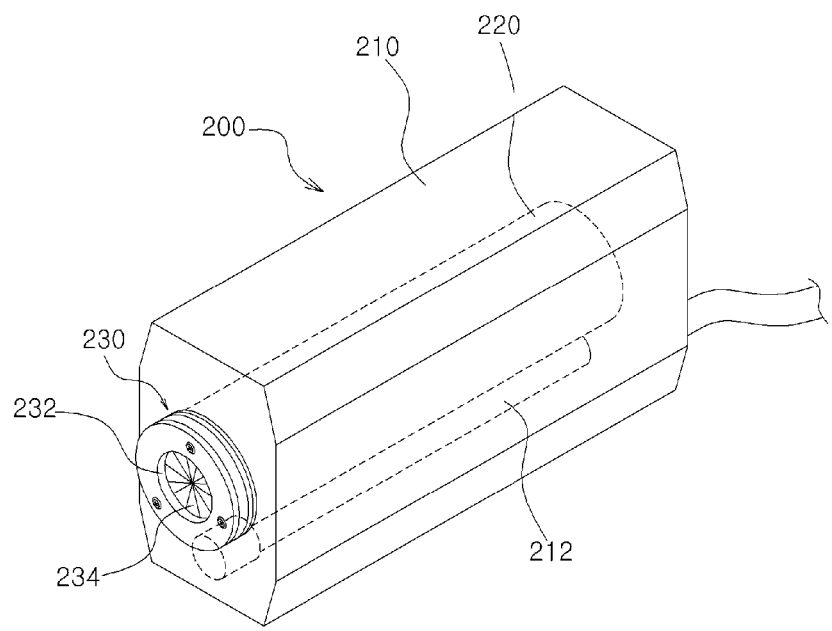

U.V. STERILIZER FOR DENTAL HANDPIECE

TECHNICAL FIELD

The present invention relates to a sterilizer for a handpiece contaminated by contacting dirt such as blood or spit, which contains germs or bacteria while being put into a patient's mouth and treating, at a dental clinic.

BACKGROUND ART

Generally, at a dental clinic, several medical appliances such as tweezers, probes, mirrors, and handpieces are used to treat teeth or gums inside a mouth. These appliances are easily contaminated by germs or bacteria contained in blood, spit or tissues of patients, so that preventing other patients from being infected with germs or bacteria by sterilizing the contaminated appliances thoroughly after use is important. Tweezers, probes, and mirrors are relatively cheap, so that it is possible to prepare them in a larger number, gather separately the once used ones, and sterilize using antiseptic solution, or steam or water of high temperature. However, handpieces, connected to a pneumatic device or a laser generator, are not so cheap as to be prepared in a large number and changed whenever being used, and equipped with pneumatic motors and lenses, so that it is impossible to sterilize using steam or water of high temperature, making it hard to sterilize.

An ultraviolet sterilizer shown in FIG. 7 was developed to sterilize such handpieces. The conventional sterilizer 100 like this is equipped in one body with a casing assembly 110 attaching an ultraviolet lamp 112 inside, a drawer 120 withdrawn from and inserted into the front side of the casing assembly 110 to put in dental appliances, and a ventilating fan 130 installed at the inside rear of the case 110 to circulate the inside air through multiple ventilating holes 132.

The sterilizer 100 has problems in that the handle of the drawer 120 is contaminated since the drawer is opened and closed by a contaminated hand to put the handpiece in the drawer 120, and the hands are contaminated by the handle of the drawer 120 when withdrawing the handpiece after sterilization, therefore the handpiece is contaminated when the handpiece is handled by the contaminated hand, together with a problem radiating ultraviolet rays outside.

As depicted in FIG. 8, another conventional sterilizer 200 which solved the problems of the drawer type sterilizer is configured in one body, installing an ultraviolet lamp 212 around a quartz tube 220 established horizontally inside the casing assembly 210 and an opening 230 closed by an ultraviolet barrier 234, which has insertion holes 232 incised in a radial shape, at the outer front of the casing assembly 210 installed with the quartz tube 220.

In case of the sterilizer 200 with an incised ultraviolet barrier 234, the ultraviolet barrier 234 is contaminated by the contaminated handpiece when the handpiece is inserted in the sterilizer, and the handpiece is contaminated by the contaminated ultraviolet barrier 234 again when the sterilized handpiece is withdrawn.

DISCLOSURE OF INVENTION

Technical Problem

The present invention has been made in order to solve the above problems occurring in the prior art, and it is an object of the invention to provide an ultraviolet sterilizer for handpieces, which prevents the sterilizer itself from being contaminated by dirt.

The area where ultraviolet rays are irradiating inside a sterilizer always maintains sterilized states, but the outside of a sterilizer where the ultraviolet rays are not reached should be kept away from dirty materials. That is, when inserting a contaminated handpiece in a sterilizer, it needs the outer portion of a sterilizer which is not sterilized by ultraviolet rays not being contacted with the contaminated handpiece.

Another object of the invention is to provide an ultraviolet sterilizer, in which, being prevented from contacting with the outside of the sterilizer when withdrawn after sterilization, the sterilized hygienic handpiece is not contaminated by the sterilizer.

Another object of the invention is to provide a sterilizer for handpieces, which has the effect of aroma therapy at the same time.

Another object of the invention is to provide a sterilizer for handpieces comprising a file tray, which can be sterilized with dental clinic files put on it by ultraviolet rays.

Another object of the invention is to provide a sterilizer for handpieces, which prevents ultraviolet rays harmful to the human body from emitting outside the sterilizer.

Technical Solution

In order to accomplish the above object, according to one aspect of the present invention, there is provided a sterilizer for dental handpieces. The sterilizer for dental handpieces includes: a casing assembly having an opening formed at the front side for coming in and going out of a handpiece; a door configured such that an ultraviolet barrier incised in a radial shape opens and closes the front opening of the casing assembly; a transparent tube installed inside the casing assembly in order to be fluid-communicatively connected with the door to put a handpiece thereon; a sensor installed on the brim of the opening at the front side of the casing assembly; an ultraviolet lamp installed inside the casing assembly; a control circuit for controlling the overall operation of the sterilizer in such a manner that it opens the ultraviolet barrier when it confirms the approach of the handpiece by the sensor, closes the ultraviolet barrier after the handpiece has been entered, turns on the ultraviolet lamp for a pre-determined time, turns off the lamp, opens the ultraviolet barrier again, and closes the ultraviolet barrier after the handpiece has been withdrawn; and a motor for opening and closing the door in response to a control signal generated from the control circuit.

When the handpiece approaches the opening of the casing assembly, the sensor installed on the brim of the opening detects the approach, and the control circuit opens the ultraviolet barrier of the door by running the motor. When the handpiece is inserted in the sterilizer, the control circuit runs the motor, closing the ultraviolet barrier and turning on the ultraviolet lamp. After a predetermined time, the control circuit turns off the ultraviolet lamp and opens the ultraviolet barrier running the motor in the reverse direction. When the handpiece is withdrawn after opening the ultraviolet barrier, the handpiece is not contacted with the sterilizer, thereby maintaining the sterilized clean state.

The control circuit further comprises a function which calculates the entering speed of a handpiece by the signal entered from the sensor, and controls the opening speed of the door according to the entering speed of the handpiece.

The diameter of the tip is short since a handpiece for a dental clinic is inserted deep into a mouse, and the handle held by a user is thick for easy grip. The sensor used for the invention, for example, an optical sensor, may determine the opening and closing speed of the door according to the intensity of the light entered into the optical receiver, and, even when a user puts a handpiece fast into a sterilizer, the opening speed of a barrier also becomes faster, thereby a handpiece not being contacted with a barrier.

In addition, it is desirable to comprise more a function calculating the thickness of a handpiece by the signal entering from a sensor and controlling the opening speed of a door according to the thickness of a handpiece.

In another embodiment of the invention, a sterilizer for dental handpiece includes: a casing assembly having an opening formed at the front side for coming in and going out of the handpiece; a door configured such that the ultraviolet barrier incised in a radial shape opens and closes the front opening of the casing assembly, and the ultraviolet barrier is opened while waiting and after completion of sterilization, and the ultraviolet barrier is closed while sterilizing; a transparent tube installed inside the casing assembly in order to be fluid-communicatively connected with the door to put a handpiece thereon; a sensor installed around the transparent tube inside the casing assembly; an ultraviolet lamp installed inside the casing assembly; a control circuit controlling the overall operation of the sterilizer in such a manner that it closes the ultraviolet barrier when the entrance of the handpiece has been confirmed by the sensor, turns on the ultraviolet lamp for a predetermined time and turns off the lamp, and opens the ultraviolet barrier again; and a motor for opening and closing the door in response to a control signal generated from the control circuit.

The ultraviolet barrier of the sterilizer for a dental handpiece is opened while waiting and after sterilization, so the handpiece can be entered into the sterilizer without touching the ultraviolet barrier. When the handpiece rests in the transparent tube inside the sterilizer, the sensor installed around the transparent tube senses the handpiece, and the control circuit closes the ultraviolet barrier running the motor and turns on the ultraviolet lamp. After a predetermined time, the control circuit turns off the lamp and opens the ultraviolet barrier running the motor again. Through the operations mentioned above, the dental sterilizer of the present invention guarantees the handpiece not being touched with the sterilizer.

The handpiece sterilizer according to the invention is equipped with a reflection protector, in which the transparent tube and the ultraviolet lamp are inserted, inside the casing assembly to protect the leakage of ultraviolet rays.

The intensity of ultraviolet rays accomplishing the sterilizing objectives is so high that ultraviolet rays leaking out of the sterilizer do harm for human body. Therefore, to prevent in advance ultraviolet rays from leaking through the chasms of the casing assembly of the handpiece, the transparent tube and the ultraviolet lamp are wrapped by the reflection protector.

Generally, it is reported that minimum 3400 $\mu W \cdot s/Cm^2$ and maximum 22000 $\mu W \cdot s/cm^2$ of energy are needed to sterilize virus and germs 100 percent. For example, dysentery bacillus is sterilized at 3400 $\mu W \cdot s/cm^2$ of ultraviolet ray energy, influenza virus is at 6600 $\mu W \cdot s/cm^2$, and tetanus bacillus is at 6600 $\mu W \cdot s/cm^2$. Therefore, maintaining 22000 $\mu W \cdot s/cm^2$ of irradiation amount of ultraviolet rays inside the sterilizer is effective. In the present invention, 13000 $\mu W \cdot s/cm^2$ of irradiation amount was observed as the result of energy measurement at a point 2 cm apart from a 9W ultraviolet lamp, so that most of germs and viruses known present can be exterminated sterilizing with two ultraviolet lamps for one second.

The handpiece sterilizer according to the invention further comprises a ventilating fan at one side of the casing assembly to exhaust the heat generated by ultraviolet lamps. In case when a handpiece sterilizer is used continuously, the temperature inside the casing assembly is increases due to the heat generated by the ultraviolet lamp. The increase of the temperature inside the casing assembly has a bad influence on the control circuit which is inside the casing assembly, therefore maintaining the temperature inside the casing assembly low by exhausting the air inside the casing assembly to the outside is desirable.

The handpiece sterilizer according to the invention may further comprise a file tray which has multiple file holes at one side of the casing assembly, which is opened and closed by a cover and can be sterilized with dental files inserted therein. The file tray is to insert tools such as a dental drill and sterilize by ultraviolet rays.

The handpiece sterilizer according to the invention can be configured more including an aromatic tray, which is a drawer putting things in and containing aromas inside, near the ventilating fan. At present, aroma therapies are known, which have various curative effects of aromas. Using aromas which have the effect of giving a sense of stability, without additional aromas specially, patients visiting a dental clinic may have mental stability, thereby obtaining favorable effects.

Advantageous Effects

According to the invention, an ultraviolet sterilizer can be prevented from being contaminated by dirt, and having a handpiece not be contacted with a sterilizer which is apt to be contaminated, a sterilized hygienic handpiece may not be contaminated by a sterilizer after sterilization.

According to the invention, the ultraviolet sterilizer does not allow the leakage of ultraviolet rays outside, provides an effect of aroma therapy as well, and sterilizes dental files at the same time.

BRIEF DESCRIPTION OF THE DRAWINGS

Further objects and advantages of the invention can be more fully understood from the following detailed description taken in conjunction with the accompanying drawings, in which:

FIG. 1 shows a perspective view of a handpiece sterilizer according to the invention;

FIG. 2 shows an exploded perspective view of a handpiece sterilizer according to the invention;

FIG. 3 shows a cross-section showing the inside of the handpiece sterilizer;

FIG. 4 shows a perspective view of the rear side of the handpiece sterilizer according to the invention;

FIG. 5 is an elevational view showing the state of the door closed;

FIG. 6 is an elevational view showing the state of the door opened;

FIG. 7 shows a conventional ultraviolet sterilizer; and

FIG. 8 shows another conventional ultraviolet sterilizer.

BEST MODE FOR CARRYING OUT THE INVENTION

The preferred embodiments of the present invention will be hereafter described in detail with reference to the accompanying drawings.

First Embodiment

FIG. 1 shows a perspective view of the handpiece sterilizer according to the invention and FIG. 2 shows an exploded perspective view of the handpiece sterilizer according to the invention. FIG. 3 shows a cross-section of the inside showing the assembled state and FIG. 4 shows a perspective view of the rear side of the handpiece sterilizer according to the invention. The casing assembly of the handpiece sterilizer 1 according to the invention is injection molded so as to be able to disassemble and assemble an upper casing 10, lower casing 10', and a door cover 20 each other. An opening 12 is formed at the front side of the lower casing 10' and the door cover. A control circuit 70 is installed at the top side of the lower casing 10' and a ventilating hole is extended to the outside from the rear upper portion, below of which a power outlet and a power switch are installed.

In FIG. 5 and FIG. 6, depicted are the opened and closed states of the door 40, which opens and closes the opening of the casing assembly by the ultraviolet barrier 46 incised in a radial shape. The door 40 is composed of a pair of door frames 44, 44', in which circular-arc-type tooth-form parts 44 engaging each other are formed respectively at one side and a frame part 42 on a semicircle which assembles an ultraviolet barrier 46 is formed at the other side, and an ultraviolet barrier 46, which is installed at the frame part 42 on the semicircle of the door frame 44, 44' and incised in a radial shape. Of the above pair of door frames 44, 44' the upper portion of one door frame 44' is fixed by a hinge so as to be able to move to the front upper portion of the door 40, and the upper portion of the other door 44 is connected to a motor M which is operated by a control circuit. When the motor starts to operate, according to the operation of the door frame 44 which is connected to the motor, the other door frame 44' is opened or closed by the tooth-form parts engaging each other.

The ultraviolet barrier 46 is to be lifted so much as not to leak rays when the handpiece is inserted, so that the ultraviolet barrier 46 needs to be formed by a flexible material like silicon or rubber, and incised in radial directions as much as not to allow leakage of rays when lifting the ultraviolet barrier 46. The ultraviolet barrier 46 may be installed at the front and the rear side of the frame part 42 on the semicircle in order to prevent leakage of ultraviolet rays more securely.

The handpiece sterilizer according to the invention is installed inside the casing assembly 10 in order to be fluid-communicatively connected with the door 40, and comprises a transparent tube 50 on which the handpiece is placed. The material of the transparent tube 50 should be endurable to heat generated by the ultraviolet lamp and anything transparent that transmits ultraviolet rays well will do.

Ultraviolet lamps 60 are installed inside the casing assembly 10, and two ultraviolet lamps of 9W capacity, in the present invention, are installed for 1 second sterilization, terminating most of the germs and viruses known up to date.

According to the invention, the handpiece sterilizer is equipped with a sensor S1 which is installed around the opening of the front side of the casing assembly 10 and detects the approach of the handpiece. A light emitter and a light receiver are installed in opposite sides around the front opening, and the light receiver receiving the light emitted from the light emitter located at the opposite side. When the handpiece approaches, the intensity of the light received at the light receiver decreases, and the control circuit opens the ultraviolet barrier 46 of the door 40, judging that the handpiece is approaching if the intensity of the light received at the light receiver decreases. The diameter of the tip is short since a handpiece is generally inserted deep into a mouth, and the handle held by a user is thick for easy grip, so that, observing the change of the intensity of the light entering into the light receiver, the ultraviolet barrier 46 is opened fast if the intensity changes fast, and the door of the ultraviolet barrier 46 is opened slowly if the intensity changes slowly.

The control circuit 70 is also desirable to observe the intensity of the light entering into the light receiver of the sensor, calculate the thickness of the handpiece, and control the speed of the opening speed of the door according to the thickness of the handpiece.

After putting the handpiece in the transparent tube 50, the sensor does not detect the change of the intensity of the light, thus the control circuit 70 closes the ultraviolet barrier 46, judging that entering process has been completed. When the ultraviolet barrier 46 is closed completely, the control circuit turns on the ultraviolet light 60, turns off the ultraviolet light 60 after a predetermined time, and opens the ultraviolet barrier 46 by starting the motor.

When the intensity of the light received by the light receiver becomes high again, the control circuit confirms the withdrawal of the handpiece from the sterilizer, and then closes the ultraviolet barrier 46.

To confirm the completion of the entering process of the handpiece into the sterilizer, a special sensor also may be installed around the transparent tube 50.

Second Embodiment

In the second embodiment according to the invention, the casing assembly, the transparent tube, the ultraviolet lamp, and the motor are same compared with the embodiment 1, but the order of door 40 closing, which is operated by the location of sensors and the control circuit, is different.

The second embodiment has differences, compared with the first embodiment in that, the door is configured to be open while the ultraviolet barrier incised in the radial shape is waiting and after the completion of the sterilizing, and the sensor is installed around the transparent tube which is inside the casing assembly and detects the approach of the handpiece. In addition, the difference is in the control circuit, which closes the ultraviolet barrier when the completion of the entering process of the handpiece is detected by the sensor, turns on the ultraviolet lamp for a predetermined time then turns off, and opens the ultraviolet barrier again by starting the motor when sterilization has been completed.

Since the ultraviolet barrier of the handpiece sterilizer is open always except while sterilizing, the possibility to contaminate the sterilizer may be completely removed when the handpiece is coming in and going out the sterilizer.

If a reflection protector 80, in which the transparent tube 50 and the ultraviolet lamp 60 is inserted, is installed inside the casing assembly in addition to the handpiece sterilizer explained in the above embodiment 1 and 2, ultraviolet rays, harmful to the human body, can be prevented from leaking outside the sterilizer. The reflection protector 80 is configured so that the inner surface wrapping the transparent tube 50 and the ultraviolet lamp 60 may reflect light effectively, thus every corner of the handpiece is sterilizes by the ultraviolet rays emitted from the ultraviolet lamp 60 and reflected, and the irradiation amount of ultraviolet rays can be increased as well.

In addition, a ventilating fan P may be desirably installed at one side of the casing assembly of the handpiece sterilizer explained in the above first and second embodiments to exhaust the heat generated by the ultraviolet lamp.

A drawer 90 is installed around the ventilating fan to put in aromas 92, emitting fragrance, which has the effect of aroma therapy, outside the sterilizer, thereby a patient may have mental stability.

If the handpiece sterilizer is configured more including a file tray 30 which has multiple file holes 15 at one side of the casing assembly, which is opened and closed by a cover 16 and can be sterilized with dental files inserted therein, dental files also can be sterilized conveniently using ultraviolet rays.

INDUSTRIAL APPLICABILITY

The present invention relates a sterilizer for sterilizing dental handpieces and files promptly and perfectly. More specifically, the invention relates a sterilizer for handpieces, which provides an effect of aroma therapy and prevents ultraviolet rays, harmful to the human body, from leaking outside the sterilizer.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A sterilizer for dental handpieces comprising:
   a casing assembly having an opening formed at the front side for coming in and going out of a handpiece;
   a door configured such that an ultraviolet barrier incised in a radial shape opens and closes the front opening of the casing assembly;
   a transparent tube installed inside the casing assembly in order to be fluid-communicatively connected with the door to put a handpiece thereon;
   a sensor installed on the brim of the opening at the front side of the casing assembly;
   an ultraviolet lamp installed inside the casing assembly;
   a control circuit for controlling the overall operation of the sterilizer in such a manner that it opens the ultraviolet barrier when it confirms the approach of the handpiece by the sensor, closes the ultraviolet barrier after the handpiece has been entered, turns on the ultraviolet lamp for a predetermined time, turns off the lamp, opens the ultraviolet barrier again, and closes the ultraviolet barrier after the handpiece has been withdrawn; and
   a motor for opening and closing the door in response to a control signal generated from the control circuit.

2. The sterilizer for dental handpieces according to claim 1, wherein the control circuit further comprises a function of calculating the entering speed or thickness of a handpiece by the signal entering from the sensor and controlling the opening speed of the door according to the calculated value.

3. The sterilizer for dental handpieces according to claim 2, wherein a reflection protector for preventing the leakage of ultraviolet rays is installed inside the casing assembly, in which the transparent tube and the ultraviolet lamp are inserted.

4. The sterilizer for dental handpieces according to claim 2, further comprising a ventilating fan provided at one side of the casing assembly, for exhausting the heat generated by ultraviolet lamps.

5. The sterilizer for dental handpieces according to claim 2, further comprising a file tray having multiple file holes provided at one side of the casing assembly, the file tray being opened and closed by a cover and being sterilized with dental files inserted therein.

6. The sterilizer for dental handpieces according to claim 2, further comprising an aromatic tray near the ventilating fan, wherein the aroma tray is received in a drawer fashion and contains aromas inside.

7. The sterilizer for dental handpieces according to claim 1, wherein a reflection protector for preventing the leakage of ultraviolet rays is installed inside the casing assembly, in which the transparent tube and the ultraviolet lamp are inserted.

8. The sterilizer for dental handpieces according to claim 1, further comprising a ventilating fan provided at one side of the casing assembly, for exhausting the heat generated by ultraviolet lamps.

9. The sterilizer f or dental handpieces according to claim 1, further comprising a file tray having multiple file holes provided at one side of the casing assembly, the file tray being opened and closed by a cover and being sterilized with dental files inserted therein.

10. The sterilizer for dental handpieces according to claim 1, further comprising an aromatic tray near the ventilating fan, wherein the aroma tray is received in a drawer fashion and contains aromas inside.

11. A sterilizer for dental handpieces comprising:
   a casing assembly having an opening formed at the front side for coming in and going out of the handpiece;
   a door configured such that the ultraviolet barrier incised in a radial shape opens and closes the front opening of the casing assembly, and the ultraviolet barrier is opened while waiting and after completion of sterilization, and the ultraviolet barrier is closed while sterilizing;
   a transparent tube installed inside the casing assembly in order to be fluid- communicatively connected with the door to put a handpiece thereon; a
   sensor installed around the transparent tube inside the casing assembly;
   an ultraviolet lamp installed inside the casing assembly;
   a control circuit controlling the overall operation of the sterilizer in such a manner that it closes the ultraviolet barrier when the entrance of the handpiece has been confirmed by the sensor, turns on the ultraviolet lamp for a pre-determined time and turns off the lamp, and opens the ultraviolet barrier again; and
   a motor for opening and closing the door in response to a control signal generated from the control circuit.

12. The sterilizer for dental handpieces according to claim 11, wherein a reflection protector for preventing the leakage of ultraviolet rays is installed inside the casing assembly, in which the transparent tube and the ultraviolet lamp are inserted.

13. The sterilizer for dental handpieces according to claim 11, further comprising a ventilating fan provided at one side of the casing assembly, for exhausting the heat generated by ultraviolet lamps.

14. The sterilizer for dental handpieces according to claim 11, further comprising a file tray having multiple file holes provided at one side of the casing assembly, the file tray being opened and closed by a cover and being sterilized with dental files inserted therein.

15. The sterilizer for dental handpieces according to claim 11, further comprising an aromatic tray near the ventilating fan, wherein the aroma tray is received in a drawer fashion and contains aromas inside.

* * * * *